US009050009B2

(12) United States Patent
Den Heeten et al.

(10) Patent No.: US 9,050,009 B2
(45) Date of Patent: Jun. 9, 2015

(54) MAMMOGRAPHY-APPARATUS

(75) Inventors: Gerard Johan Den Heeten, Amsterdam (NL); Cornelis Antonius Grimbergen, Abcoude (NL)

(73) Assignee: Academisch Medisch Centrum bij de Universiteit van Amsterdam, Amsterdam (NL)

( * ) Notice: Subject to any disclaimer, the term of this patent is extended or adjusted under 35 U.S.C. 154(b) by 336 days.

(21) Appl. No.: 13/565,003

(22) Filed: Aug. 2, 2012

(65) Prior Publication Data
US 2013/0028373 A1 Jan. 31, 2013

Related U.S. Application Data

(63) Continuation of application No. PCT/NL2011/050095, filed on Feb. 10, 2011.

(30) Foreign Application Priority Data

Feb. 19, 2010 (NL) .................................. 2004270
Jul. 26, 2010 (NL) .................................. 2005159
Oct. 13, 2010 (NL) .................................. 2005509

(51) Int. Cl.
*A61B 6/04* (2006.01)
*A61B 6/00* (2006.01)

(52) U.S. Cl.
CPC ............... *A61B 6/0414* (2013.01); *A61B 6/502* (2013.01); *A61B 6/507* (2013.01)

(58) Field of Classification Search
CPC .................................. A61B 6/502; A61B 6/04
USPC ..................... 378/37, 165, 166, 208
See application file for complete search history.

(56) References Cited

U.S. PATENT DOCUMENTS

| 5,335,257 A | 8/1994 | Stunberg |
| 6,694,173 B1 | 2/2004 | Bende et al. |
| 7,656,993 B2 | 2/2010 | Hoernig |
| 7,734,013 B2 * | 6/2010 | Kashiwagi et al. ........... 378/108 |

(Continued)

FOREIGN PATENT DOCUMENTS

| EP | 1493380 | 1/2005 |
| WO | WO-9727801 | 8/1997 |
| WO | WO-0117424 | 3/2001 |

OTHER PUBLICATIONS

Khamapirad, T., "Diagnostic Imaging of Breat Cancer with LOIS: clinical feasibility", *International Society for Optical Engineering, SPIE-INT*, vol. 5697, No. 1, 2005, pp. 35-44.

(Continued)

*Primary Examiner* — Jurie Yun
(74) *Attorney, Agent, or Firm* — Peacock Myers, P.C.; Jeffrey D. Myers

(57) ABSTRACT

Mammography-apparatus for detecting malignant cells in a breast comprising an x-ray source and an x-ray detector that cooperates with the x-ray source for providing an x-ray image of said breast, and further comprising a paddle for flattening the breast by pressing it against said x-ray detector, wherein at least one sensor is applied for measuring a parameter that is used for determining the pressure at which the paddle compresses the breast, and wherein a control system is provided which controls the actuation of the paddle depending on the pressure that is applied to the breast, wherein there is a contact area measuring unit for measuring the contact area between the breast and the paddle.

19 Claims, 1 Drawing Sheet

(56) References Cited

U.S. PATENT DOCUMENTS

| | | |
|---|---|---|
| 2005/0004458 A1 | 1/2005 | Kanayama et al. |
| 2006/0262903 A1 | 11/2006 | Diebold |
| 2008/0080668 A1 | 4/2008 | Kashiwagi |
| 2008/0240346 A1 | 10/2008 | Kashiwagi et al. |
| 2008/0249415 A1 | 10/2008 | Okamura et al. |
| 2009/0262887 A1 | 10/2009 | Iordache et al. |
| 2012/0020464 A1 * | 1/2012 | Matsuura ............... 378/208 |

OTHER PUBLICATIONS

Vaartjes, Susanne E., "First Clinical Trials of the Twente Photoacoustic Mammoscope (PAM)", *International Society for Optical Engineering, Proceedings SPIE*, vol. 6629, Jun. 19, 2007, pp. 1-12.

Vaartjes, S. E., "Initial Results of in vivo Non-Invasive Cancer Imaging in the Human Breast Using Near-Infrared Photoacoustics", *Optical Express*, vol. 15, No. 19, Sep. 17, 2007, pp. 12277-12285.

* cited by examiner

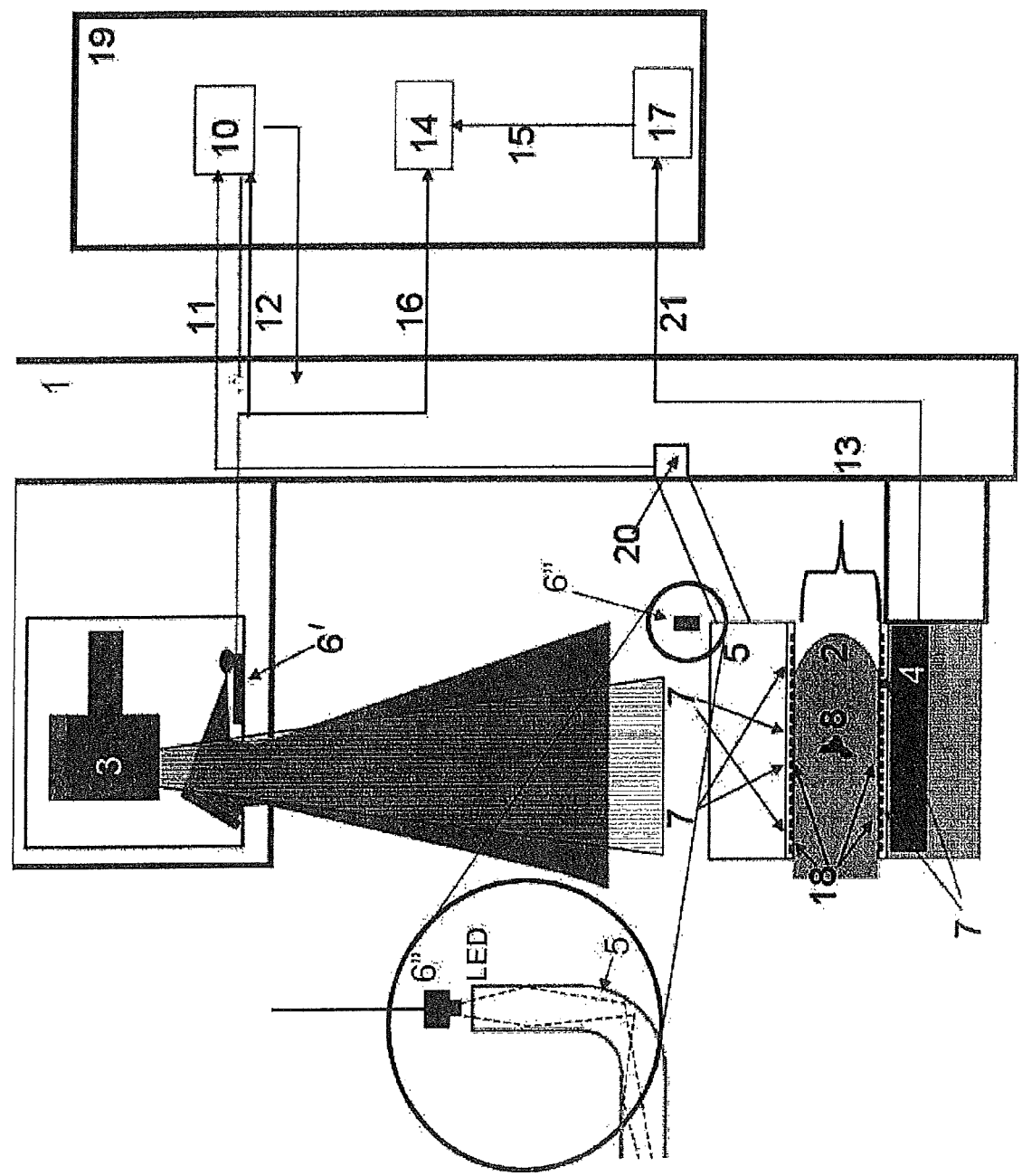

MAMMOGRAPHY-APPARATUS

CROSS-REFERENCE TO RELATED APPLICATIONS

This application is a continuation application of International Patent Application Serial No. PCT/NL2011/050095, entitled "Mammography-Apparatus", to Academisch Medisch Centrum van de Universiteit van Amsterdam, filed on Feb. 10, 2011, which is a continuation of Netherlands Patent Application Serial No. 2004270, entitled "Mammography-Apparatus", filed on Feb. 19, 2010; Netherlands Patent Application Serial No. 2005159, entitled "Mammography-Apparatus", filed on Jul. 26, 2010; and Netherlands Patent Application Serial No. 2005509, entitled "Mammography-Apparatus", filed on Oct. 13, 2010, and the specifications and claims thereof are incorporated herein by reference.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

COPYRIGHTED MATERIAL

Not Applicable.

BACKGROUND OF THE INVENTION

1. Field of the Invention (Technical Field)

The invention relates to a mammography-apparatus for detecting malignant cells in a breast comprising an x-ray source and an x-ray detector that cooperates with the x-ray source for providing an x-ray image of said breast, and further comprising a paddle for flattening the breast by pressing it against said x-ray detector, wherein at least one sensor is applied for measuring a parameter that is used for determining the pressure at which the paddle presses the breast, and wherein a control system is provided which controls the actuation of the paddle depending on the pressure that is applied to the breast. Pressing the breast with the paddle against the x-ray detector serves the purpose of the breast's flattening, which is desirable for getting a proper x-ray image of the breast.

2. Description of Related Art

A mammography-apparatus according to the preamble is known from U.S. Pat. No. 7,656,993. In this known mammography-apparatus the paddle is shaped according to the curvature of the breast, and the paddle comprises multiple elements that can be individually moved and controlled depending on the pressures measured with several pressure sensors in order to provide the desired pressure to the breast taking due account of the breast's physical properties.

One of the disadvantages of the known mammography-apparatus is that in order to improve the quality of x-ray imaging it is suggested to apply an uneven distribution of pressures to the breast. The general understanding in the art requires however that a uniform pressure is applied for flattening of the breast which allows the application of a lesser dose of x-rays and provides better image quality.

BRIEF SUMMARY OF THE INVENTION

A first objective of the invention is therefore to take into account specifically those parameters that are considered relevant for the quality of the x-ray imaging of the breast. Knowing these parameters and taking them into account is considered to improve establishing whether or not malignant cells are present.

A further objective of the invention is to improve the known mammography-apparatus in that unnecessary pressurization of the breast during x-ray imaging is avoided.

Still a further objective is to enhance the capability of the mammography-apparatus to reliably detect malignant cells in breast tissue.

Still a further objective is to provide an alternative for existing methods employing the known method of mammography, in which pressurization is used to further determine the presence of possibly malignant cells that are detected with the mammography-apparatus.

These and other objectives of the invention which may become apparent from the following disclosure, are at least in part addressed with the features of the mammography-apparatus of the invention as specified in the appended claims.

BRIEF DESCRIPTION OF THE SEVERAL VIEWS OF THE DRAWINGS

The invention will hereinafter be further elucidated with reference to the drawing of a mammography-apparatus in accordance with the invention.

In the drawing:

FIG. 1 shows schematically the mammography-apparatus of the invention.

DESCRIPTION OF THE INVENTION

In a first aspect of the invention the mammography-apparatus has a contact area measuring unit for measuring the contact area between the breast and the paddle. In the mammography apparatus of the invention the paddle is preferably made unitary, that means in one piece, at least without the series of adjacent paddle elements that are individually movable and controllable as in the prior art according to U.S. Pat. No. 7,656,993.

The contact area measuring unit can be used in a dual fashion. In an embodiment in which the at least one sensor is used to measure the force that is applied to the breast, this force together with the contact area provides the average pressure that is applied to the breast. This average pressure can then be controlled at a pre-established level so as to avoid un-necessary and avoidable pain during imaging.

Further, the measured contact area between the breast and the paddle resulting from the breast-compression can be used together with the pre-established force-level, to calculate and apply a specific mean compression pressure independent of the dimensions of the individual breast. Knowing and controlling this specific mean compression pressure leads to a better standardization of the mammography operation, with improved accuracy of screening whilst avoiding unnecessary pain for the persons being screened. A mean compression pressure in the order of the diastolic blood pressure avoids excessive discomfort in many cases, particularly with small breasts.

The aforesaid applies also if the at least one sensor is used to directly measure the pressure rather than the force that is applied to the breast, which is possible in an advantageous embodiment which will be discussed hereinafter.

Preferably the contact area measuring unit comprises optical means. It is then possible to measure the contact area between the breast and the paddle without interfering with the x-ray imaging. Suitably then the optical means comprises a camera, preferably a CCD camera.

One further aspect of the invention relates to such a mammography-apparatus for detecting malignant cells in a breast comprising an x-ray source and an x-ray detector that cooperates with the x-ray source for providing an x-ray image of said breast, and further comprising a paddle for flattening the breast by pressing it against said x-ray detector and a contact area measuring unit comprising optical means, preferably a camera, for measuring the contact area between the breast and the paddle and wherein the paddle is translucent. In such a mammography-apparatus it is beneficial that the paddle or a separate transparent plate which is assembled to unite with the paddle is connected to a light source, wherein said paddle or said separate transparent plate, and said light source are arranged for propagating light within the paddle or said plate and for releasing light from the paddle or said plate in the direction of the camera upon the breast tissue contacting the paddle or said plate. This provides a very effective and easy way to implement the contact area measuring unit by making use of the so-called frustrated total internal reflection effect of the light propagating in the paddle (or the plate assembled to unite with the paddle) when the paddle (or said plate) is in contact with the breast. The amount of light as well as the area from which light escapes the paddle (or from said separate plate) depends on the (local) pressure applied by the breast on the paddle c.q. said plate. This phenomenon makes it further possible to measure the perfusion in the capillaries in the skin of the breast dependent on the (local) pressure, e.g., using speckle imaging.

Preferably the paddle and/or the separate plate assembled to unite with the paddle, is made of Lexan® polycarbonate resin. Lexan is a registered trademark of the firm Sabic Innovative Plastics for an amorphous engineering thermoplastic that is-known for its outstanding mechanical, optical, electrical and thermal properties. The optical properties make the material very suitable for providing an effective optical path between the contact area measuring unit and the breast which is under investigation. The optical properties of the polycarbonate resin can be further improved by supplying same with traces of titaniumoxide. It is also possible to cover the paddle and/or the separate plate with graphene, which is known for its strength, translucency and its excellent behavior in conducting electricity and heat.

The known mammography-apparatus is provided with a processing unit for processing data from the x-ray detector and converting it into an x-ray image of the breast. Preferably this processing unit and the contact area measuring unit are connected to an estimator for determining a ratio between the con-tact area between the breast and the paddle, and a breast cross-section as derived from the x-ray image of the breast. Also this ratio may provide information that is relevant for establishing the presence of malignant cells.

Preferably the mammography-apparatus has a thickness measuring unit for measuring the breast thickness whilst said breast is compressed and flattened by the paddle. The breast thickness during compression, which needs not only be steady state information but may also include information regarding the breast thickness at several levels of compression, is a parameter that together with the applied force provides information on the mechanical properties of the breast. By measuring this parameter, nonlinearities in the mechanical properties of the breast tissue that may be an indication of malignant cell growth, can be detected.

Suitably the thickness measuring unit is embodied with means to detect a distance between the paddle and the x-ray detector, in particular a distance between the region of the paddle that contacts the breast and the x-ray detector. This is a straightforward manner to determine the thickness of the breast that is being flattened between the paddle and the x-ray detector.

It is further desirable that the mammography-apparatus has pressure sensors that are distributed in the paddle and/or the x-ray detector so as to register local pressures in the breast. For one thing this provides the possibility that the pressure sensors are connected to the processing unit, which then can correlate said local pressures with the x-ray image of said breast. This local pressure information is indicative for the breast cross-section during its compression, and the combined information of the local pressures with the x-ray image of the breast increases the reliability of detecting the presence of malignant cells.

It is also possible to directly use these pressure sensors for controlling the actuation of the paddle depending on the thus measured pressure that is applied to the breast.

The reliability of detecting the presence of malignant cells may be even further enhanced in a preferred embodiment of the mammography-apparatus of the invention, wherein the paddle and/or x-ray detector comprises temperature sensors for registering a temperature distribution of the breast surface whilst it is flattened between the paddle and the x-ray detector. Also the temperature distribution of the breast surface is usable information which may be used for determining the breast contact area with the paddle during compression, as well as for detecting the presence of malignant cells per se. The feature that the temperature sensors are provided in the paddle and/or x-ray detector provides the advantage that the sensors are—due to the breast's deformation—closer to the heat producing cells and blood vessels in the breast, and the physical contact of the breast with the paddle and/or x-ray detector improves heat transfer to the temperature sensors, reducing the time needed to reach a steady state situation.

It is envisaged that best results in analyzing the information from the temperature distribution in the breast can be obtained when the temperature sensors are connected to the processing means, and that said processing means are arranged to correlate the temperature distribution of the breast with the x-ray image.

Most preferably the pressure sensors and/or temperature sensors are transparent for x-rays. In this way the quality of the x-ray image from the breast does not suffer from the application of the pressure sensors and/or temperature sensors.

In another embodiment wherein the sensors are not transparent, it is preferred that the paddle and/or the x-ray detector and the pressure sensors and/or temperature sensors provided therein exhibit substantially the same level of absorption for x-rays. The effect on the x-ray imaging is then limited to the need to apply a slightly higher energy level of the x-rays.

In still another embodiment wherein the sensors are not transparent and wherein a processing unit is applied for providing the x-ray image, it is preferred that the processing unit is arranged to remove the image of the pressure sensors and/or temperature sensors from the x-ray image.

The inventors consider that the pressure sensors and/or the temperature sensors preferably include thin film sensors and/or Fiber Bragg grating sensors. As well as being sensitive to strain, the Bragg wavelength of Fiber Bragg grating sensors is also sensitive to temperature. The measured strain can be converted to the pressure that is applied to the paddle and/or the x-ray detector.

An advantage of thin film sensors and Fiber Bragg grating sensors is that they are optically transparent and to a large extent translucent for x-rays, and that in as far they do absorb x-rays, the material of the paddle and/or x-ray detector can easily be selected with approximately the same absorption value. If there still remain noticeable images of the fibers in the x-ray image of the breast, these images of the fibers can easily be subtracted from the x-ray image of the breast. The optical transparency of the fiber Bragg grating sensors is beneficial for positioning the breast between the paddle and the detector for the x-ray imaging.

Is further preferred that the Fiber Bragg grating sensors are distributed in the paddle and/or the x-ray detector in a preselected number so as to provide a resolution of approximately 8×8 pixels, or at least 6×6 pixels. This provides sufficient information which can meaningfully be related to the x-ray image of the breast.

DETAILED DESCRIPTION OF THE INVENTION

With reference to FIG. 1 the mammography-apparatus of the invention is denoted with reference 1. This mammography-apparatus 1 is used for screening malignant cells 8 in a breast 2. For this purpose the mammography-apparatus 1 comprises an x-ray source 3 and an x-ray detector 4 that cooperates with the x-ray source for providing an x-ray image of said breast 2.

The mammography-apparatus 1 further comprises a paddle 5 for flattening the breast 2 by compressing it against said x-ray detector 4. In the embodiment shown the paddle 5 is provided with a force- or torque sensor 20 for measuring a force at which the paddle 5 flattens the breast 2. Further a control system 10, normally forming part of a computer system 19, is provided that receives the measurement signals of the force or torque sensor 20 via line 11, and controls the actuation of the paddle 5 via a steering line 12 depending on the force that is measured with the sensor 20 and using the results of the contact area measurement which is discussed in the next paragraph.

In controlling the actuation of the paddle 5, the force measured with sensor 20 is first converted to a pressure by taking into account the contact area between the paddle 5 and the breast 2. For this purpose a contact area measuring unit 6', 6" is applied for measuring the contact area between the breast 2 and the paddle 5. The contact area measuring unit 6', 6" comprises optical means such as a camera 6', preferably a CCD camera. The output of a CCD camera 6' can be directly available in a digital format for control system 10.

Beneficially the optical means 6', 6" of the contact area measuring unit comprises further a light source 6", whereby the paddle 5 is connected to this light source 6", and said paddle 5 and light source 6" are arranged for propagating light within the paddle 5 and for releasing light from the paddle 5 in the direction of the camera 6' upon the breast 2 tissue contacting the paddle 5.

To improve the optical path from the contact area measuring unit 6', 6" to the breast 2, it is advantageous to make the paddle of Lexan® polycarbonate resin. Lexan® is a registered trademark of the firm Sabic Innovative Plastics for an amorphous engineering thermoplastic that is known for its outstanding mechanical, optical, electrical and thermal properties. The optical properties of the polycarbonate resin can be further improved by supplying same with traces of titanium oxide. Although not shown in FIG. 1, it is also possible to measure the contact area using a separate plate that is assembled to unite with the paddle on the side of the paddle which is intended to contact the breast. In this embodiment the plate is then connected to the light source, and the plate and light source are then arranged for propagating light within the plate and for releasing light from the plate in the direction of the camera upon the breast tissue contacting the plate.

The mammography-apparatus of the invention further has a processing unit 17 for processing data from the x-ray detector 4 received through line 21 and converting it into an x-ray image of the breast 2. The processing unit 17 and the contact area measuring unit 6', 6" are connected via respective lines 15, 16 to an estimator 14 in the computer system 19 for determining a ratio between the contact area measured between the breast 2 and the paddle 5, and a breast cross-section as derived from the x-ray image of the breast 2.

The mammography-apparatus 1 further has a thickness measuring unit 13 for measuring the breast thickness whilst said breast 2 is flattened by the paddle 5. The thickness measuring unit 13 is embodied to detect a distance between the region of the paddle 5 that contacts the breast 2, and the x-ray detector 4. In the example shown this may be an angle measuring unit connected to the arm that holds the paddle 5.

The paddle 5 is preferably provided with a series of pressure sensors 7 for measuring local pressures which may be indicative for the presence of malignant cells. It is desirable that the pressure sensors 7 are distributed in the paddle 5 and preferably also in the x-ray detector 4 so as to register local pressures in the breast 2, and that the processing unit 17 (usually forming part of the computer system 19) is arranged to correlate said local pressures with the x-ray image of said breast 2. It is also possible that the pressure sensors 7 are directly employed for controlling the pressure that is applied to the breast 2. In this way a force sensor for measuring the force at which the paddle 5 is applied to the breast 2 may be dispensed with.

FIG. 1 further shows that the paddle 5 and/or x-ray detector 4 comprises temperature sensors 18 for registering a temperature distribution of the breast 2 whilst it is pressurized between the paddle 5 and the x-ray detector 4. These temperature sensors 18 for registering a temperature distribution of the breast 2 are preferably measuring during the whole period of compression of the breast 2 by the paddle 5. Preferably the processing unit 17 of the computer system 19 is also arranged to correlate the temperature distribution of the breast 2 with the x-ray image.

The above elucidation of the features of the invention are not intended to limit the appended claims to the specific example that is provided herewith. On the contrary, it is possible that many variations are feasible within the scope of the invention. It is for instance preferred that the pressure sensors 7 and/or temperature sensors 18 are transparent for x-rays. In another embodiment however it is feasible that the paddle 5 and/or the x-ray detector 4 and the pressure sensors 7 and/or temperature sensors 18 provided therein exhibit substantially the same level of absorption for x-rays. In still another embodiment it is feasible that the pressure sensors 7 and/or the temperature sensors 18 are not fully transparent for x-rays, and that the processing unit 17 is arranged to remove the image of the pressure sensors 7 and/or temperature sensors 18 from the x-ray image.

What is claimed is:

1. Mammography-apparatus for detecting malignant cells in a breast, said apparatus comprising an x-ray source and an x-ray detector that cooperates with the x-ray source for providing an x-ray image of said breast, and further comprising a paddle for flattening the breast by pressing it against said x-ray detector, wherein at least one sensor is applied for measuring a parameter that is used for determining a pressure at which the paddle compresses the breast, and wherein a control system is provided which is receivingly connected to said sensor and to a contact area measuring unit for measuring a contact area between the breast and the paddle, and which control system controls an actuation of the paddle depending on the pressure that is applied to the breast as established with the said at least one sensor and said contact area measuring unit in combination.

2. Mammography-apparatus according to claim 1, wherein the contact area measuring unit comprises optical means.

3. Mammography-apparatus according to claim 2, wherein the optical means comprises a camera.

4. Mammography-apparatus for detecting malignant cells in a breast, said apparatus comprising an x-ray source and an x-ray detector that cooperates with the x-ray source for providing an x-ray image of said breast, and further comprising a paddle for flattening the breast by pressing it against said x-ray detector, and which has a contact area measuring unit comprising optical means for measuring a contact area between the breast and the paddle, wherein the paddle is translucent, and wherein the paddle or a separate transparent plate assembled to unite with the paddle is connected to a light source, wherein said paddle or said separate transparent plate, and said light source are arranged for propagating light within the paddle or said separate plate and for releasing light from the paddle or said separate plate in the direction of said optical means upon the breast tissue contacting the paddle or said separate plate for measuring said contact area between the breast and the paddle.

5. Mammography-apparatus according to claim 4, wherein the paddle is made of polycarbonate resin.

6. Mammography-apparatus according to claim 5, wherein the polycarbonate resin comprises traces of ti-taniumoxide.

7. Mammography-apparatus according to claim 4, provided with a processing unit for processing data from the x-ray detector and converting it into an x-ray image of the breast, wherein the processing unit and the contact area measuring unit are connected to an estimator for determining a size ratio between said contact area and a breast cross-section as derived from the x-ray image from the breast.

8. Mammography-apparatus according to claim 4, wherein said apparatus has a thickness measuring unit for measuring the breast thickness whilst said breast is compressed by the paddle.

9. Mammography-apparatus according to claim 8, wherein the thickness measuring unit is embodied with means to detect a distance between the paddle and the x-ray detector.

10. Mammography-apparatus according to claim 4, wherein the paddle is unitary and there are pressure sensors that are distributed in the paddle and/or the x-ray detector so as to register local pressures in the breast.

11. Mammography-apparatus according to claim 10, wherein the paddle and/or x-ray detector comprises temperature sensors for registering a temperature distribution of the breast whilst it is flattened between the paddle and the x-ray detector.

12. Mammography-apparatus according to claim 11, wherein the pressure sensors and/or the temperature sensors are connected to a processing unit, and said processing unit is arranged to correlate local pressures in the breast and/or the temperature distribution of the breast with the x-ray image.

13. Mammography-apparatus according to claim 11, wherein the pressure sensors and/or temperature sensors are transparent for x-rays.

14. Mammography-apparatus according to claim 11, wherein the paddle and/or the x-ray detector and the pressure sensors and/or temperature sensors provided therein exhibit substantially the same level of absorption for x-rays.

15. Mammography-apparatus according to claim 11, wherein a processing unit is applied for providing the x-ray image, characterized in that the pressure sensors and/or the temperature sensors are non-transparent for x-rays, and that the processing unit is arranged to remove the image of the pressure sensors and/or temperature sensors from the x-ray image.

16. Mammography-apparatus according claim 11, wherein the pressure sensors and/or the temperature sensors include thin film sensors and/or Fiber Bragg grating sensors.

17. Mammography-apparatus according to claim 16, characterized in that the Fiber Bragg grating sensors are distributed in the paddle and/or the x-ray detector in a preselected number so as to provide a resolution of at least 6x6 pixels.

18. Mammography-apparatus for detecting malignant cells in a breast, said apparatus comprising an x-ray source and an x-ray detector that cooperates with the x-ray source for providing an x-ray image of said breast, and
further comprising a paddle for flattening the breast by pressing it against said x-ray detector,
wherein the paddle is unitary and there are pressure sensors that are distributed in the paddle and/or the x-ray detector so as to register local pressures in the breast due to the paddle compressing the breast, and
wherein a control system is provided which is receivingly connected to said pressure sensors, which control system controls an actuation of the paddle depending on a pressure that is applied to the breast as measured with said sensors.

19. Method of operating a mammography-apparatus according to claim 18, wherein a mean compression pressure is applied to the breast in the order of a diastolic blood pressure so as to avoid excessive discomfort, particularly with a small breast.

* * * * *